(12) United States Patent
Labrousse et al.

(10) Patent No.: US 11,931,204 B2
(45) Date of Patent: Mar. 19, 2024

(54) CATHETER AND ASSOCIATED METHODS

(71) Applicants: Louis Marc Jean Lucien Labrousse, Bordeaux (FR); Lionel Jean Pierre Leroux, Bordeaux (FR)

(72) Inventors: Louis Marc Jean Lucien Labrousse, Bordeaux (FR); Lionel Jean Pierre Leroux, Bordeaux (FR)

( * ) Notice: Subject to any disclaimer, the term of this patent is extended or adjusted under 35 U.S.C. 154(b) by 396 days.

(21) Appl. No.: 17/471,818

(22) Filed: Sep. 10, 2021

(65) Prior Publication Data

US 2021/0401403 A1 Dec. 30, 2021

Related U.S. Application Data

(62) Division of application No. 15/113,592, filed as application No. PCT/EP2015/051190 on Jan. 22, 2015, now Pat. No. 11,141,133.

(30) Foreign Application Priority Data

Jan. 22, 2014 (FR) ...................................... 1450513

(51) Int. Cl.
| | |
|---|---|
| A61M 25/01 | (2006.01) |
| A61B 8/00 | (2006.01) |
| A61B 8/08 | (2006.01) |
| A61B 8/12 | (2006.01) |
| A61B 17/04 | (2006.01) |
| A61M 25/04 | (2006.01) |
| A61M 25/09 | (2006.01) |
| A61N 7/00 | (2006.01) |
| A61N 7/02 | (2006.01) |

(52) U.S. Cl.
CPC ............ *A61B 8/445* (2013.01); *A61B 8/0883* (2013.01); *A61B 8/12* (2013.01); *A61B 17/0491* (2013.01); *A61M 25/0102* (2013.01); *A61M 25/04* (2013.01); *A61M 2025/018* (2013.01); *A61M 25/09* (2013.01); *A61M 2025/09116* (2013.01); *A61N 7/00* (2013.01); *A61N 7/02* (2013.01)

(58) Field of Classification Search
CPC .............. A61B 8/445; A61M 25/0102; A61M 2025/018
See application file for complete search history.

(56) References Cited

U.S. PATENT DOCUMENTS

| | | |
|---|---|---|
| 6,592,520 B1 | 7/2003 | Peszynski |
| 2001/0021841 A1 | 9/2001 | Webler |
| 2004/0068191 A1 | 4/2004 | Seward et al. |
| 2008/0177183 A1 | 7/2008 | Courtney |

(Continued)

OTHER PUBLICATIONS

International Search Report as issued in International Patent Application No. PCT/EP2015/051190, dated Apr. 29, 2015.

*Primary Examiner* — Colin T. Sakamoto
(74) *Attorney, Agent, or Firm* — Pillsbury Winthrop Shaw Pittman LLP

(57) ABSTRACT

A catheter includes a hollow body which extends longitudinally and has at least one first side window and a probe emitting a wave beam, the first side window allowing the radiation of the beam in a region next to the catheter for generating imaging, the catheter also including a longitudinal guiding device allowing a transmission of a movement to an intervention element, the intervention element moving in at least an area of the beam, the intervention angle between the first intervention element and the axis of the catheter being controlled by a remote control system.

7 Claims, 9 Drawing Sheets

(56) References Cited

U.S. PATENT DOCUMENTS

2009/0088648 A1  4/2009  Jaffe et al.
2009/0093726 A1  4/2009  Takayama
2011/0021911 A1  1/2011  Waters et al.
2014/0187939 A1  7/2014  Ogawa

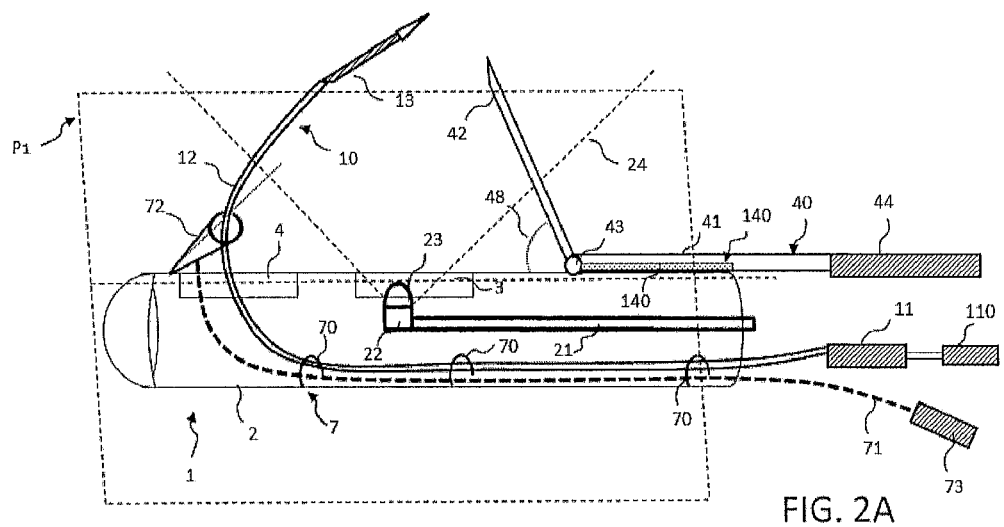
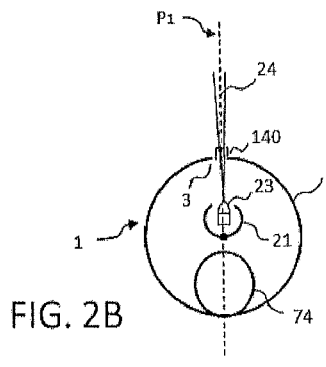 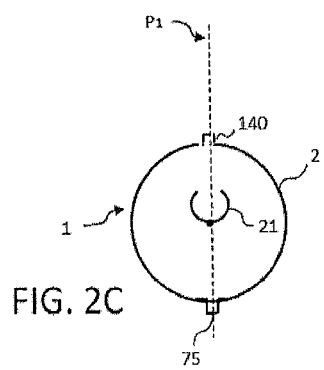 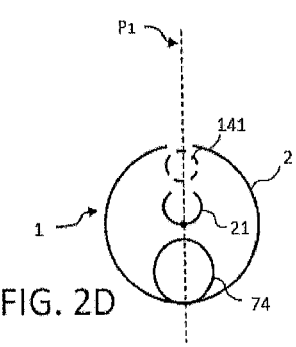
FIG. 2A
FIG. 2B  FIG. 2C  FIG. 2D

CATHETER AND ASSOCIATED METHODS

CROSS-REFERENCE TO RELATED APPLICATIONS

This application is a divisional of U.S. application Ser. No. 15/113,592, filed Jul. 22, 2016, which is the U.S. National Stage of PCT/EP2015/051190, filed Jan. 22, 2015, which in turn claims priority to French Patent Application No. 1450513, filed Jan. 22, 2014. The entire contents of all applications are incorporated herein by reference in their entireties.

FIELD

The field of the invention relates to catheters. More particularly, the field of the invention relates to the field of the catheters for heart interventions which require an accurate operation to be performed while visualizing the operation performed in real time. Finally, the field of the invention is concerned with flexible or rigid catheters that can be introduced in the human body percutaneously, through intravascular routes, or that can be directly introduced by a puncture of a heart cavity, such as the atrium or ventricle, or even through a vascular axis such as a pulmonary vein.

STATE OF THE ART

Currently, there are catheters to visualize areas of the heart during an operation requiring a visual control of the area to be operated on. There are also catheters including an intervention element to operate on an area of the heart. Typically, an intervention element allows for example a clip laying to be made on a valve. There are more complex operations, for example annuloplasty operations aiming at strengthening sealing, setting the size or reducing the ring for inserting the mitral or tricuspid valve.

During such operations, many instruments are necessary. It is sometimes necessary to introduce different catheters to conduct different operations on an organ of the heart such as a valve.

Risks related to such operations are dramatically reduced when a visualization of the operations can be rendered in real time. One drawback of the current solutions is that the probes are often located outside the body and require a recording of the images of the heart through the thorax. The images undergo a degradation inherent to the structure of the body through which the waves pass, adjoining organs causing wave reflections, artefacts caused by fat or lungs and spurious echoes of the reflected waves. Further, it is difficult to properly dispose the probe with respect to the operation to be conducted and depending on the orientation of the intervention element.

When an ultrasonic probe is introduced into the organ, herein the heart or in the proximity thereof, an overall space problem rises. Indeed, the operation areas are confined in small dimension spaces and it is difficult to convey, in addition to the medical instruments, probes allowing the operation conducted on a part of an organ to be visualized.

Some devices enable a probe to be integrated, but the latter are often of large dimensions and are difficult to handle in combination with a handling of other instruments. Generally, they do not offer the entire necessary flexibility and impose a defined orientation of the catheter when introduced, which may not be compatible with the operating mode.

Indeed, the operations generally conducted at the right or left atrioventricular valves demand a great accuracy and a certain manoeuvrability providing flexibility to the catheter. Some operations, such as leak treatment, suturing, annuloplasty, etc., remain difficult to be conducted because the catheter is difficult to position and to stabilize to perform successfully an operation under visual control.

As regards methods for intervening on right or left atrioventricular valves and associated operating modes, many drawbacks result from the absence of a catheter enabling an accurate image of the operations conducted on an organ to be obtained.

The reference treatment in repairing the right or left atrioventricular valves indeed associates an action on the valve itself and an action on the valve annulus, called annuloplasty. The latter action consists in "setting the size and tightening" the valve annulus either by the use of a suture along this annulus, or by the placement of a prosthetic annulus having a suitable size which is directly sutured in contact with the valve annulus. The percutaneous and/or mini-invasive treatment of the mitral and tricuspid valvular pathologies essentially relies on actions made on the leaflets, as for example for laying one or more Mitraclips and one or more Neochords.

The current limit in the percutaneous or mini-invasive mitral annuloplasty devices comes from the difficulty to perform reproducibly, reliably and securely the placement of sutures exactly at the valve annulus.

The difficulties related to the placement of such sutures come from the difficulty to visualize very accurately the valve annulus whether it is in transthoracic or transoesophageal echocardiography. Indeed, its anatomic relations both with the ventricle and the atrium make the placement of sutures potentially risky in terms of atrial or ventricular perforation, of failure of engagement of the valve annulus into the suture, that is the risk of embrittlement of the suture, and for the mitral commissural anterior region the risk of aortic perforation.

SUMMARY OF THE INVENTION

The invention aims at overcoming the abovementioned drawbacks.

One object of the invention relates to a catheter comprising a hollow body extending longitudinally. The catheter of the invention includes at least one first side window and a probe emitting a wave beam, said first side window allowing the beam to be radiated in a region lateral to the catheter for generating imaging, said catheter further comprising a longitudinal guiding device allowing a movement to be transmitted to an intervention element, said intervention element moving in at least one area of the beam, the angle between said first intervention element and the axis of the catheter, called an "intervention angle", being driven by a remote driving means.

One advantage is the possibility of having an intervention element in a zone which can be visually controlled during an operation. The intervention element is advantageously rotatably drivable by a remote driving means. The catheter of the invention thus allows an accuracy gain and a range of movement of an intervention element in a viewable area.

Advantageously, the side radiation area of the beam is substantially included in a first plane. According to one embodiment, the probe is an ultrasonic probe. The ultrasonic probe enables the ultrasonic beam to be emitted and received. It is connected outside to the command console and enables the signal to be processed and the images it generates to be visualized. The first window is advantageously an ultrasonic window, that is not filtering the ultrasonic waves.

One advantage is to allow a visualization in the plane of the beam of the operations conducted by the intervention element(s) itself (themselves) remotely driven by a means for controlling its (their) position and/or its (their) orientation in the plane of the beam. Such a control means can comprise a control handle.

The side window is particularly suitable for the operations on the valves of the heart and/or annulus at the base thereof. The catheter is preferentially introduced between the atrium and the ventricle and allows the operations conducted on the annulus and on the valve to be accurately visualized.

An advantage of a planar radiation is the increased accuracy of visualization. It enables an alignment to be obtained by construction between the visualization window and the movements of the intervention elements.

Advantageously, the catheter comprises a second longitudinal guiding device enabling at least one arm of a removable probe to be directed inside the hollow body of the catheter and enabling the probe to be positioned facing the first window.

According to one embodiment, the probe is able to move longitudinally in the hollow body and is associated with a holding device enabling the stability of the probe to be provided when positioned facing the first window.

One advantage is that the catheter can be an interchangeable consumable.

According to another embodiment, the probe is attached to the hollow body.

Advantageously, a deformable element is movable in the first plane P1 by means of a guiding device, the deformable element being adapted to cooperate with an intervention element at its distal end.

Advantageously, the intervention element is attached and guided to the distal end of the deformable element through a distal arm.

Advantageously, the deformable element includes a sheath, said intervention element being introduced inside the sheath. The intervention element and/or the end of the deformable element are guided in the plane of the beam.

Advantageously, at least one angular guiding device is associated with at least one longitudinal guiding device so as to initiate a rotational movement to drive the intervention angle, the rotational movement being initiated by a remote driving means.

Advantageously, the rotational movement causes the rotation of a distal mobile arm of the angular guiding device guiding either the distal end of a deformable element, the intervention element, or the whole formed by the distal end of a deformable element and an intervention element.

Advantageously, the remote driving means enable a translational movement of an arm of the angular guiding device to be converted into a rotational movement of a distal movable arm.

Advantageously, the translational movement of an arm of the angular guiding device is carried out by means of a longitudinal guiding device.

Advantageously, at least one remote driving means comprises a handle or a plunger wheel the rotation of which allows the aperture of the intervention angle of the intervention element to be driven.

Advantageously, at least one longitudinal guiding device comprises either a longitudinal port, arches, or a rail, wherein the rail can be inside or outside the catheter and integral with the latter.

Advantageously, at least one longitudinal guiding device enables all or part of an angular guiding device and/or a deformable element and/or an intervention element to be longitudinally guided.

Advantageously, at least one longitudinal guiding device comprises a longitudinal port extending inside the catheter, said longitudinal guiding device being associated at its distal end with an angular guiding device and being held in a plane P1 comprising the axis of the catheter.

Advantageously, the deformable element is flexible and is introduced in the longitudinal port through the proximal end of the catheter, the hollow body of the catheter comprising a side aperture the largest dimension of which is included in the same plane as the largest dimension of the first window, said side aperture being adapted to allow the rotational movements of an angular guiding device and the passenger of at least one intervention element outside the catheter.

Advantageously, a deformable element is guided by an angular guiding device comprising a push rod translating on a longitudinal guiding device integral with the catheter, the translation of the push rod actuating a pivot connection of the angular guiding device, the push rod being actuated by the remote driving means, the pivot connection initiating a rotation of a distal movable arm supporting an intervention element.

Advantageously, the longitudinal guiding device comprises a rail integral with the body of the catheter extending longitudinally in the first plane P1 and allowing the push rod of the angular guiding device to be translated.

Advantageously, at least one angular guiding device includes a wire allowing a distal movable arm to be held in a closed position, a pivot connection of the angular guiding device being coupled to a return element exerting a restoring force tending to open the intervention element in the plane of the beam, an action on the wire allowing the intervention element to be pivoted in the plane of the beam.

Advantageously, at least one angular guiding device includes a wire allowing a distal movable arm to be held in an open position, a pivot connection of the angular guiding device being coupled with a return element exerting a restoring force tending to close the intervention element along the catheter, an action on the wire allowing the intervention element to be pivoted in the plane of the beam.

Advantageously, the catheter comprises a first deformable element and a second deformable element respectively associated with a first and a second intervention elements, two angular guiding devices associated with two longitudinal guiding devices, both intervention elements respectively opening into downstream and upstream of the first window such that a first intervention element and respectively a second intervention element can advance in the plane of the beam simultaneously or successively.

Another object of the invention relates to a catheter comprising a hollow body extending longitudinally, characterized in that it includes at least three guides aligned in a first plane P1, which are collinear to the axis of the catheter, a first guide able to guide longitudinally a removable probe and a second and a third guides being each able to guide at least longitudinally an angular guiding device and/or a deformable element and/or an intervention element, the first guide opening into a first side window of the body of the catheter, the second guide opening into upstream of the window and the third guide opening into downstream of the window, the catheter further comprising at least one steerable angular guiding device associated with one of the second or third guides and the rotational movements of which are included in the first plane P1.

Advantageously, the catheter comprises at least one side aperture the largest dimension of which is included in the same plane as in the largest dimension of the first side window, the second or the third guide opening onto the side aperture of the catheter.

Advantageously, at least one of the second and/or third guide(s) comprises a longitudinal rail integral with the body of the catheter.

Advantageously, one of the second and/or third guide(s) comprises a tubular port extending longitudinally inside the hollow body of the catheter.

Advantageously, the catheter comprises at least one deformable element cooperating with at least one angular guiding device.

Advantageously according to the different objects of the invention, the catheter includes an irrigation channel inside the catheter the flow rate of an irrigation fluid of which can be controlled by means of a fluid control device.

Advantageously, according to the different objects of the invention, the catheter is able to cooperate with an introducer including a suction cap at its proximal end to adhere by suction to an organ to be perforated, said introducer including an operating channel enabling said catheter to pass inside said organ.

Advantageously, the suction cap comprises a centre operating channel not communicating with the suction part of the suction cap.

Advantageously, the suction cup is associated with a device allowing the longitudinal mobilization of the catheter through the suction cup, as well as the side movements of the catheter through the suction cup to be controlled by tightening.

Another object of the invention relates to a method for intervening on an atrioventricular valve of the heart by means of the catheter of the invention. The method comprises:
  placing and stabilizing the catheter so as to dispose the first window of the catheter facing an intervention area in the proximity of an area of the atrioventricular valve;
  moving at least one intervention element of the catheter in the intervention area;
  operating on the atrioventricular valve or the annulus located at its base, said operation being conducted by means of visualizing an imaging from the ultrasonic probe of the catheter.

Advantageously, the introduction of the ultrasonic probe is made before the catheter is placed in the proximity of the region of the atrioventricular valve.

Advantageously, the method comprises a preliminary step of introducing the catheter:
  either through an atrial antegrade route of the heart allowing the catheter to come from the heart atrium;
  or through a ventricular retrograde route of the heart enabling the catheter to come from the heart ventricle.

According to a particular embodiment, the method comprises:
  firstly perforating the annulus by a first intervention element;
  introducing a wire through the first intervention element in the perforated point;
  recovering the wire on the other side of the valve through the second intervention element;
  rotating the catheter about the longitudinal axis of the catheter;
  secondly perforating the annulus through an intervention element;
  introducing the wire by one of the intervention elements;
  recovering the wire on the other side of the valve through the other intervention element;
  tightening the annulus by bringing the perforated points of the annulus closer.

According to a second particular embodiment, the method comprises:
  firstly perforating the valve at the end thereof by a first intervention element;
  introducing a wire through the first intervention element in the perforated point;
  recovering the wire on the other side of the valve through the second intervention;
  attaching the wire at a point of the inner or outer wall of the heart through the second intervention element.

BRIEF DESCRIPTION OF THE FIGURES

Further characteristics and advantages of the invention will appear upon reading the detailed following description, in reference to the appended figures, which illustrate:

FIG. 1A: a longitudinal view of a catheter according to a first embodiment of the invention in a profile view comprising a deformable element and the longitudinal and angular guiding devices associated with the deformable element;

FIGS. 2A, 2F: a catheter according to a second embodiment of the invention comprising two deformable elements and the associated longitudinal and angular guiding devices;

FIGS. 2B to 2E: cross-section views of the section of a catheter according to the invention according to different alternative embodiments of longitudinal guiding device;

DESCRIPTION

Figure 1B:
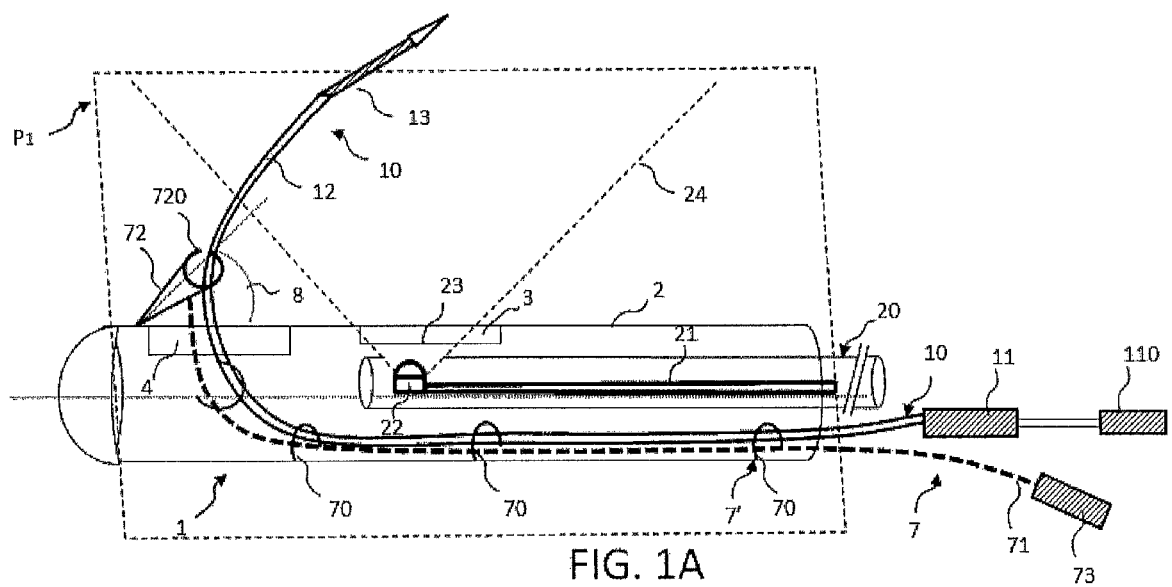
FIGS. 1B to 1D: cross-section views of the section of a catheter according to the invention according to different alternative embodiments of the longitudinal guiding means.
Figure 1B:
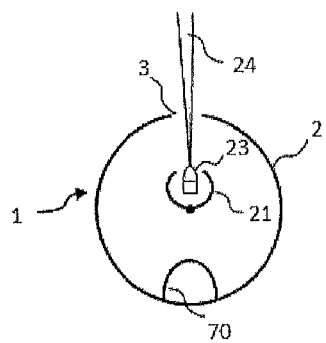

In the following of the description, by "catheter", it is meant a medical device comprising a tube having variable width and flexibility and manufactured with different materials according to the models or uses intended therefor.

The catheter is intended to be inserted:
  either in a cavity of the body, the cavity can be natural or made by a chirurgical procedure;
  or in a blood vessel.

The catheter can either be intended to drainage or infusion of liquids, or can even allow the access to one or more medical devices or allow the introduction of imaging devices.

A flexible introducer can thus be intended in the present description as a catheter enabling other medical instruments to be introduced.

By "side aperture" of the catheter, it is intended an aperture with the meaning of a window enabling waves of an imaging probe to pass therethrough. In the case of the use of an ultrasonic probe, the aperture is an ultrasonic window. The aperture can be a mechanical aperture made in the body of the catheter. The aperture can further be covered with a removable or attached cover, as a vitreous element, not filtering the ultrasonic waves of the probe.

By "longitudinal port", it is intended a tubular or equivalently shaped guide disposed inside the catheter and extending longitudinally in its hollow body enabling a deformable element or a probe or an intervention element to pass therethrough.

FIG. 1A represents one embodiment of the invention. A catheter 1 comprises a hollow, for example tubular body 2, in which an ultrasonic probe 23 is introduced through a proximal port of the catheter and can move longitudinally in the hollow body. In one embodiment, the body 2 is a flexible sheath for example for percutaneous applications. According to another mode, the body is rigid, for example for surgical applications such as directly introducing the catheter 1 in one of the ventricles of the heart or in one of the right or left atria during a surgical procedure.

Probe

In one embodiment, the probe 23 comprises a longitudinal guiding device 20 guiding an arm 21 which can be flexible or rigid depending on the combination contemplated with the body 2 of the catheter 1. The probe 23 comprises a transducer allowing a wave beam to be emitted in a cone 24 and the echoes of the emitted and reflected waves to be received as well as making it possible to transfer to an external command and visualization console the data enabling the ultrasonographic image to be made up. The cone is preferentially substantially planar. A side ultrasonic window, represented as a side aperture 3, designed in the body 2 of the catheter 1 allows a radiation to be emitted from the emitter 23 outside the catheter 1 towards an organ to be lighted.

The head 22 of the probe is preferentially oriented so as to emit a beam parallel to the longitudinal axis of the catheter 1. Preferentially, the plane comprising the beam comprises the longitudinal axis of the catheter 1.

The analysis of the echoes enables a real time imaging to be precisely obtained. Since the ultrasonography is localized, the obtained images enable an accurate representation of some organs of the body such as a mitral or tricuspid valve, its annulus as well as the surrounding anatomic structures to be obtained.

According to one embodiment, the probe is an ultrasonic probe comprising ultrasound cells. The beam thus generated is an ultrasonic beam. The number and the arrangement of the cells of the probe can be configured depending on the contemplated application. For example, the probe can comprise a few cells or 16, 32, 64 or more cells. The cells are arranged longitudinally or as a matrix.

According to one embodiment, the emitter 23 can be held in a fixed position inside the body 2 of the catheter 1 so as to direct the beam outwardly from the catheter through the window 3. To do this, holding means can be used as, for example, an abutment disposed inside the body 2 or a screw tightening along the body 2 of the catheter 1.

When the probe 23 is directly attached inside a catheter 1 without being removable, the emitter is integral with the body 2 of the catheter 1. The catheter of the invention can for example be an imaging catheter comprising an integral imaging ultrasonic probe.

According to one alternative embodiment which can be combined with the holding means, a device for rotating the entire end of the catheter 1 along its longitudinal axis can be installed inside the catheter 1. This rotation device enables the orientation of the head 22 of the ultrasonic probe 23 to be controlled. The entire end of the catheter 1 comprises in this embodiment: the ultrasonic probe and at least one of the areas enabling a deformable element and/or an intervention element to pass therethrough. Such a device for rotating along the longitudinal axis is described in the following by means of the control of two guiding wires.

Beam

According to one preferred embodiment of the invention, the emitting cone 24 of the probe 23 is substantially included in a plane P1. In the latter case, the cells of the probe are preferentially longitudinally arranged. The limitation of the imaging area to an area substantially included in a plane enables an accurate image to be obtained in the beam. On the other hand, if an intervention element of the catheter is guided in the plane of the beam, the knowledge of its radial position is structurally known. Further, the obtained images enable the movements of such an intervention element to be accurately followed in the plane inside the organ.

Figure 1C:
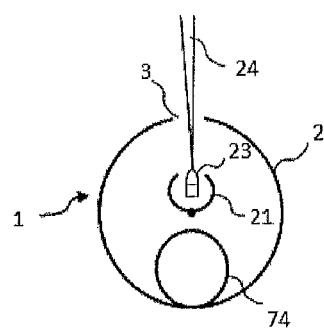
Figure 1D:
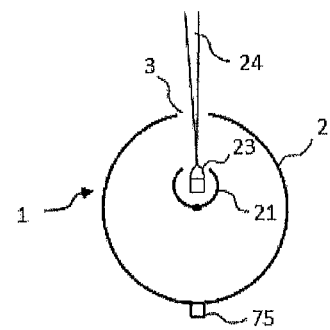

The plane P1 of FIG. 1A represents the plane comprising the beam 24. FIGS. 1B, 1C and 1D represent a section of the catheter 1, the cross-section being made at the window 3. These figures also represent the plane of the beam 24 which comprises a small aperture.

According to one embodiment of the invention, the beam 24 can have a widthwise aperture angle perpendicular to the longitudinal axis of the catheter 1 of a few degrees. The "widthwise aperture angle" in the present description is more simply called an "aperture angle". The latter aperture remains considered substantially close to a beam included in a plane when the aperture is lower than 15°. The beam is in this case directive enough to allow a very accurate imaging to be generated.

In addition to its side aperture, the beam can have longitudinal aperture angles adapted to angularly extend on either side the beam longitudinally along the axis of the catheter 1. For example, an angle of 45° with the longitudinal axis of the catheter 1 enables the coverage of the beam to be extended beyond the distal and proximal ends of the ultrasonic window. The longitudinal aperture can be flared for example if the probe is domed. The longitudinal aperture of the beam can be identical on either side of the ultrasonic window, that is on the distal edge and the proximal edge of the ultrasonic window.

A "plane lateral" to the catheter 1 is a plane the dimensions of which extend longitudinally to the catheter 1. The side plane is parallel to the axis of the catheter 1. It preferentially comprises the axis of the catheter 1, but according to another embodiment, it could also be slightly oblique and/or oriented to the axis of a radius of the circle formed by a transverse cross-section of the catheter 1.

In one alternative embodiment, the probe is configured to obtain an aperture lower than 10°. This aperture is thus also considered substantially close to a plane. The plane of beam 24 can be obtained:

either by the emission of a wave beam in a plane by means of an adapted emitter;
  or by the limitation of the slot shaped window 3 which allows waves emitted along a plane comprising the longitudinal axis of the catheter 1 to pass therethrough.

The planar beam 24 can comprise a certain tolerated width of a few millimetres given that at a certain distance of a few centimetres, the beam widens because of its aperture.

The advantage of the generation of a planar beam is that it allows the number of cells necessary in the probe to be reduced. For example, each emitter/receiver can be a piezoelectric ceramics. The cells used can be arranged as a reduced matrix of cells for example of a longitudinal shape. This option enables the overall space of an emitter to be reduced and allows a probe to be integrated into a catheter 1 with the flexible body 2. Indeed, the generation of a local image along a main, here longitudinal dimension, enables the number of necessary cells to be dramatically reduced while preserving a high definition image. This is a considerable advantage here for the on-board probes in particular in flexible catheters intended to be percutaneously or intravenously introduced.

According to one embodiment of the invention, the elements generating the ultrasonic beam are arranged as a matrix enabling a so-called three-dimension or 3D imaging to be obtained. One or more piezoelectric cells can be used for these purposes.

Deformable Elements

According to the invention, a first deformable element 10, which forms a flexible arm, enables an intervention element 13 to be guided. A means 11 for driving the movements of the deformable element allows for example movements away from the intervention element 13 at the distal end of the catheter to be carried out. The deformable device can comprise in one embodiment a distal arm 12 adapted to corporate with the intervention element 13. The distal end of the deformable element 10 is more generally called in the following of the invention a "distal arm" 12. An angular guiding device 7 enables the intervention angle 8 to be controlled and the intervention element 13 or the distal arm 12 of the deformable element 10 to be guided in the plane of the beam 24.

According to one embodiment of the invention, a deformable element 10 is an angiographic catheter type sheath. According to another embodiment of the invention, a deformable element is a rail on which the intervention element will slide.

The distal deformable arm 12 of the deformable element 10 enables the intervention element 13 to be guided in the plane of the beam 24. Further, the intervention element 13 can be longitudinally inserted into the deformable element 10 from its proximal region and come out more or less totally at its distal end. The intervention element 13 can be introduced in the deformable element and guided by a handle 110.

According to one embodiment, the first deformable element 10 is introduced in the hollow cavity of the body 2 of the catheter 1 having a port at its proximal end. The distal arm 12 can be guided in its angular orientation 8 by means, for example, of an angular guiding device 7 a distal movable part 72 of which comprises in this example an a ring 720. The "distal movable part" 72 is called in the following of the description a "distal movable arm" 72 of the angular guiding device 7. The same name is determined for the distal movable arm 42 of the second angular guiding device 40 shown in FIG. 2A.

The angular guiding device 7 is associated with a longitudinal guiding device 7' here represented as rings in the example of FIG. 1.

The distal moveable arm 72 of the angular guiding device is controllable by a main arm 71 and a handle 73. By way of example, the control can be performed by actuating a pivot connection or by modifying the length of a wire 41' using the handle 73. The angle 8, which substantially defines the intervention angle, that is the angle of attack of the intervention element 13 in the beam 24 is thus adjustable.

a—Intervention Element

The intervention element 13 makes it possible to intervene on a part of an organ in order to hold it, insert therein or suture an implantable device or sew it for example. The intervention element 13 is located in an area that can extend from a few millimetres from the surface of the catheter 1 to a few centimetres, or even about ten centimetres.

The intervention element 13 can be a needle or a radiofrequency needle, an electrical recording probe, "biopsy forceps" or a gripping forceps for example. Further, the intervention element can also be a puncture element, an angiography probe, a balloon probe, a guide, a laser probe, a lasso enabling a guide or a wire to be recovered, a device allowing a clip of a suture or a fastener or even a heat delivering or temperature lowering element to be attached. A heat delivering element can be for example a radiofrequency probe and a lowering temperature element can be for example a cryode probe. The intervention elements can allow points, fasteners, clips to be attached. Further, they can enable intravascular sutures to be made or an implantable device such as a prosthetic annulus or a valve substitute to be attached.

According to one embodiment, the intervention element 13 uses a deformable element 10 and/or an angular guiding device having a distal moveable arm 72 to be mobilized in the ultrasonic beam 24.

According to another embodiment, the intervention element 13 is mobilisable because of its own properties and does not use the deformable element and/or the angular guiding device.

A needle enables the annulus of a valve to be perforated. This operation enables, for example, a wire to be introduced in the aperture made. One advantage of the invention is to allow an accuracy gain upon handling such a needle with a dimension of a few tenths millimetres at the tip thereof.

Another possibility is to have a spring element between two apertures made on an annulus from a puncture needle. This operation enables, for example, two points of the circumference of an annulus of a valve to be tightened and thus the perimeter of the annulus to be decreased.

c—Guiding Device

Two types of guiding devices are described and associated in this invention.

a longitudinal guiding device;

an angular guiding device.

Depending on the configurations, both longitudinal and angular guiding devices cooperate by having elements common or not so as to allow displacements of the intervention element in the plane of the beam 24.

The catheter 1 can comprise, depending on the embodiments, one or more longitudinal guiding device(s) along the main axis of the catheter 1.

The longitudinal guiding device(s) can be in the form of rings, rail, sheath or port, combined or not, located in the port of the catheter 1. Advantageously, the same longitudinal guiding types can be located outside the body of the catheter 1.

As regards the longitudinal guiding device, depending on the embodiments of the invention, it makes possible the guiding of at least one of the following elements:

the ultrasonic probe;

and/or an angular guiding device when the same includes an arm for actuating a pivot connection as the element 72;

and/or a deformable element and/or an intervention element along the catheter 1;

and/or a deformable element and/or an intervention element along the main arm and/or the movable distal arm of the angular guiding device.

The longitudinal guiding device(s) can be implemented along the catheter 1 according to different alternative embodiments represented in a non-limiting way in FIGS. 1A, 1B, 1C, 1D, 2A, 2B, 2C, 2D, 2E and 2F.

As regard the angular guiding device(s), they allow the mobilization if needs be of the flexible distal arm 12 of the deformable element 10 and/or if needs be of the intervention element 13 in the plane of the ultrasonic beam 24.

According to one an embodiment, the angular guiding device 7 comprises
- a distal movable arm 72, which directs the angular rotation 8 of the deformable element 10 or of its distal arm 12 and/or the intervention element 13;
- a main arm 71 enabling the distal movable arm 72 to be driven;
- a remote driving means 73 enabling the main arm 71 to be acted on.

Figure 3A:
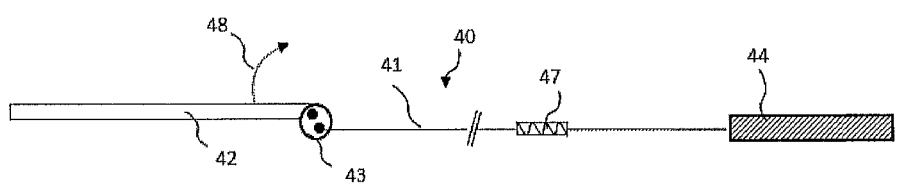
FIGS. 3A, 3B, 3C, 3D: different alternatives of a longitudinal guiding device associated with an angular guiding device of a catheter of the invention enabling an intervention element to be actuated.

It can also to be defined according to two other modes:
- a first mode is represented in FIG. 3A by a push rod 41 the translation of which actuates a pivot connection 43, the push rod being actuated by the remote driving means 44, the pivot connection 43 initiating a rotation of the distal movable arm 42 acting as a support and enabling the deformable element (not represented) and/or the intervention element (not represented) to be mobilized in an area of the plane of the beam 24.

In this first mode, the push rod 41 can be intended as well as an element of a longitudinal guiding device given the translation movement and cooperating with the pivot connection 43 and distal movable arm 42 or as an element of an angular guiding device given that it is an element actuating the pivot connection 43. It can be combined with another longitudinal guiding device enabling an intervention element 13 using the arm 42 as a support to be conveyed.

Figure 4A:
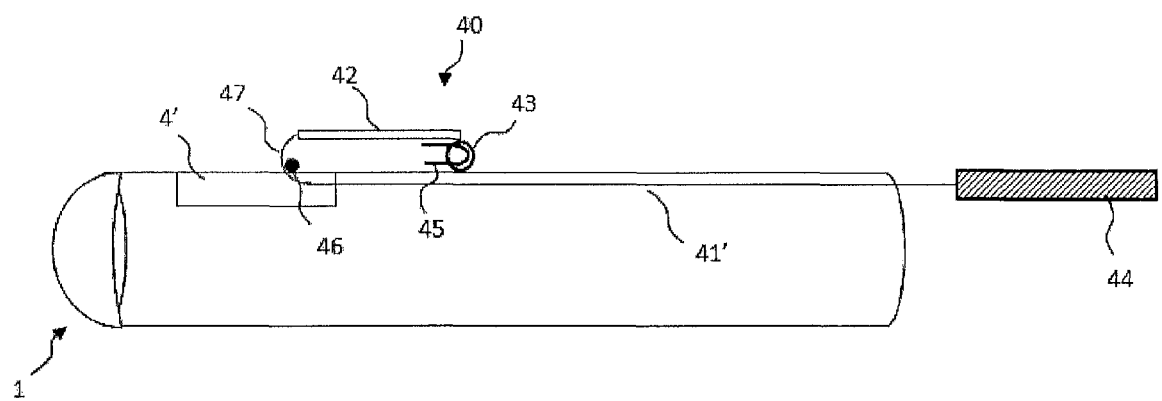
FIGS. 4A, 4B: a catheter comprising an intervention element driven from a deformable element and an angular guiding device.
Figure 4B:
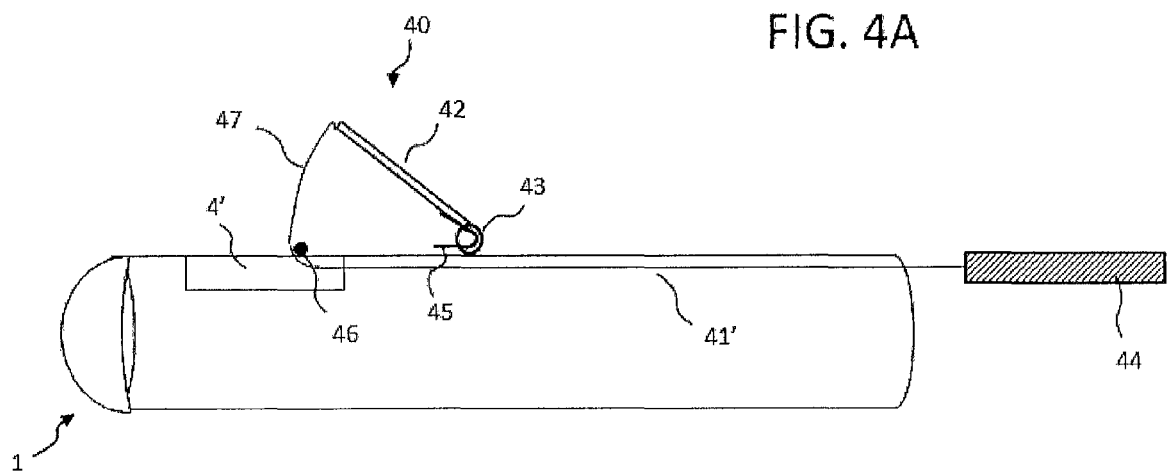

The arm 42 forming a support to an intervention element can also be directly an intervention element.
- a second mode is represented in FIGS. 4A and 4B in which a distal movable arm 42 is combined with elements 43, 45 of a second angular guiding device 40 for angularly controlling said distal movable arm 42. The second angular guiding device 40 comprises a return element 43 exerting a restoring force and a wire 41' including a portion 47 external to the catheter 1.

Four alternatives are described in FIGS. 4A, 4B.

In the same way, the movable arm 42 can be intended as a support for a deformable element 10' or a support for an intervention element 13' but also as the intervention element itself according to the embodiment contemplated.

The wire 41' can be intended as a longitudinal guiding device in that it carries out a translation along the longitudinal axis of the catheter 1 or as an element of the angular guiding device given that it actuates the rotation by releasing the arm 42. It can be associated to another longitudinal guiding device such as a port enabling an intervention element using the arm 42 as a support to be conveyed.

In the alternative represented in FIGS. 1A and 1B, a longitudinal guiding device 70 enables the intervention element 13 to be conveyed outside the catheter 1 through a side aperture 4. According to another alternative, the aperture could be made at the distal end of the catheter at its end. The last alternative would require a further guiding element at the end of the catheter 1 to bring the intervention element back into the plane of the beam 24.

In the case of FIGS. 1B to 1D, the longitudinal guiding device 7 comprises longitudinal guiding means 70, 74, 75 inside or outside the body 2 of the catheter 1 which can be rings 70 or even a tube or a sheath 74 or an external rail 75 located on the external surface of the catheter 1. In a non-represented identical way, an internal rail in the body 2 of the catheter 1 could be made.

FIG. 1B corresponds to the case represented in FIG. 1A in which the longitudinal guiding means 70 are internal rings in which the deformable element 10 can be moved while being guided. The rings 70 enable the deformable element 10 and the intervention element 13 to be conveyed to the aperture 4 or an aperture at the distal end. The angular guiding device comprising the distal movable arm 72 makes it possible to orient:
- either the distal arm 12 of the deformable element 10;
- directly the intervention element 13;
- or naturally the deformable element 10 and/or its distal arm 12 and the intervention element 13 in the plane of the beam 24.

It is noted in FIGS. 1B, 1C and 1D, that an arm of a longitudinal guiding device 21 enables the displacements of a probe 23 to be guided.

FIG. 1C represents the case of a tube 74 making it possible to convey at least to a side aperture 4 or an aperture arranged at the distal end of the catheter 1.
- an angular guiding device including an arm for actuating a pivot connection and/or;
- a deformable element 10 and/or;
- an intervention element 13.

FIG. 1D represents the case of an external rail 75 making it possible to convey at least:
- an angular guiding device enabling a pivot connection to be actuated; or
- an arm 10 of a deformable element or;
- an intervention element 13 to the distal end of the catheter 1.

When the axis of the rail 75 is the same as the axis of the main length of the window 3 along the surface of the catheter 1, then the intervention element 13 and the deformable element 10 are upstream of the window 3, that is on the proximal part of the catheter 1 with respect to the position of the window 3. This prevents the rail 75 from passing on the window and impeding emission and reception of ultrasonic waves.

When the axis of the rail 75 is not the same as the axis of the main length of the window 3 along the surface of the catheter 1, then the rail 75 is arranged diametrically opposite the window 3 on the external surface opposite the catheter 1 (case of FIG. 1D). This imposes the deformable element 10 to be conveyed up to the distal end of the catheter 1 and the intervention element 13 to be passed about the end of the catheter 1 to come back into the plane of the beam 24. In this case, an angular guiding device 7 which is in particular the distal movable arm 72 forming a means for controlling the intervention angle 8 enables the intervention element 13 to be held in the plane of the beam 24.

In conclusion, when a rail is used, it can be arranged either in the axis of the window 3, or in a plane parallel to the main axis of the window and in the plane of the beam. It is thus necessarily diametrically opposite the main axis of the window 3.

Further, the angular guiding device 7 comprises means for controlling the introduction angle of the intervention element 13 in the plane of the beam 24 with respect to the axis of the catheter 1. Hereinafter, the "distal movable arm" refers to an element that can be more generally intended as a means for controlling the intervention angle 8.

In the example of FIG. 1A, the distal movable arm 72 of the angular guiding device 7 is attached to the catheter 1 facing the intervention window 4 enabling the deformable element 10 or the intervention element 13 to pass therethrough. The angular guiding means 7 comprising a remote driving means 73 for driving the movements of the means for controlling the angle 8 of the distal movable arm 72. It can be for example a handle 73. According to other alternative embodiments, the remote driving means 73 can be a plunger wheel attached to the catheter 1 on its proximal part. To provide the connection between the driving means 73 and the control means having distal movable arm 72 for the intervention angle 8, the guiding means can include a flexible or rigid rod 71 enabling the angle 8 to be controlled. Another embodiment could be the placement of wires 71 enabling the angle of the distal movable arm 72 to be set.

In one embodiment represented in FIG. 1A, the distal movable arm 72 enabling the intervention angle 8 to be defined is attached to the body 2 of the catheter 1 so as to facilitate guiding of the deformable element 10 and the intervention element 13 outside the catheter 1 along a given direction. The intervention element 13 is directed into an area substantially included in the same plane as the plane of the beam 24. The distal movable arm 72 provides the co-linearity of the plane 24 and of the movements of the intervention element 13. The intervention area is thus in a plane lateral to the catheter 1 which enables the intervention element 13 to be under control. The distal movable arm 72 for controlling the intervention angle 8 is steerable to enable the intervention element 13 to be oriented in the plane of the beam 24. The steerable end called a distal movable arm 72 can comprise a ring 720 in which the distal arm 12 of the first deformable element 10 or directly the intervention element 13 can be inserted. Hence, the intervention element 13 and/or the distal arm 12 of the deformable element 10 can extend in the axis of the ring 720 to go to a distance more or less close to the catheter 1.

This is an advantage to allow an intervention operation in a visually controllable area with strong accuracy requirements. One advantage of an intervention in a plane lateral to the catheter 1 is to obtain a relative stability of the intervention elements which are integral with the image acquisition system, that is the ultrasonic probe of the first window 3, when the catheter 1 is introduced.

The operator or surgeon can, depending on its visualization window, orient the intervention element 13 in the plane of the beam as he/she wishes thanks to the driving means.

According to another embodiment, the first deformable element 10 can be a rigid or flexible rod arranged at the periphery of the body 2 of the catheter 1 as represented in FIGS. 2E, 2F, 3A to 3D, 4A and 4B.

Beam and Intervention Element

When the catheter 1 is used for an operation in the heart, the beam 24 enables, in a side plane comprising the axis of the catheter 1, the annulus of a valve, for example a mitral or tricuspid valve, the valve leaflets, the sub-valvular apparatus as well as the heart muscle to be visualized. The visualization of the imaging enables an extremely accurate image to be obtained. The imaging is then used to locally intervene by means of a deformable element and an intervention element, such as the intervention element 13, for example, to attach a suture on a part of the valve, the annulus or surrounding anatomic structures.

One advantage of the emission of the beam 24, substantially included in a plane, is that the intervention area can be represented by a very accurate image. The latter is then of assistance of an intervention in particular for an operation requiring an accuracy of handling.

One advantage of the use of an ultrasonic probe combined with the catheter is that it can be calibrated and configured to obtain an image adapted to the operation contemplated. For example, a calibration adapted to an operation on a mitral or tricuspid valve can be obtained with a beam range from 1 to 5 cm allowing a local handling of the intervention element 13 in an area close to the catheter 1.

FIG. 2A represents one embodiment in which a second angular guiding device 40 is coupled to the catheter 1. The catheter 1 in one embodiment could be only equipped with the second angular guiding device 40, regardless of the practical mode, such as a push rod or a control wire, and of the probe without necessarily comprising the first angular guiding device and the first deformable element.

In this figure, the longitudinal guiding device 20 of the probe 23 is not represented although it is compatible with this embodiment.

Figure 2E:
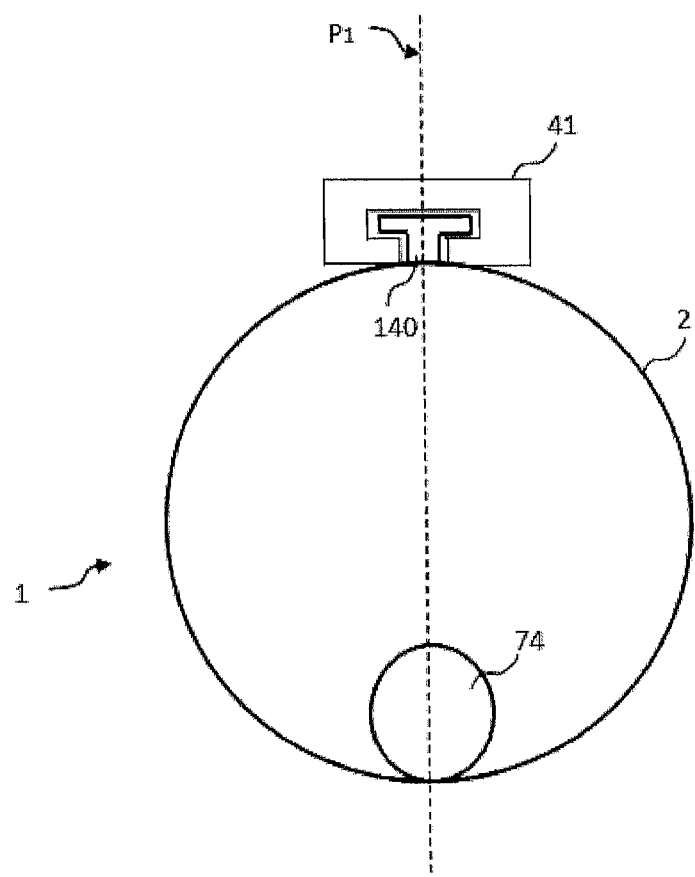

In this embodiment, the second angular guiding device 40 is attached by a longitudinal guiding device 41 on the external surface of the catheter 1. This longitudinal guiding device can be for example a rail 140 as represented in FIG. 2E. The axis of the rail 140 is the same as the average axis of the length of the window 3 so as to provide the co-linearity of the plane 24 and the range of the movements of the distal movable arm 42 of the angular guiding device and consequently of the deformable element and the intervention element which will be oriented by the distal movable arm 42.

Advantageously, the second angular guiding device 40 is removable and the driving means 44 enables the longitudinal position of the second angular guiding device 40 to be modified with respect to the ultrasonic window 3.

In this embodiment, the remote driving means 44 locally drives the movements of the arm 41, for example its translation along the catheter 1 for example if the arm 41 is a push rod. A feature of this embodiment is that the remote driving means 44 enables the intervention angle 48 to be controlled at the same time by the pivot connection 43. One advantage is a saving of overall space for the catheter 1.

It is the remote driving means 44 of the intervention angle 48 that enables the distal movable arm 42 of the second angular guiding device 40 to be hinged and the deformable element and the intervention element to be oriented in the plane of the beam at a suitable angle. The distal movable arm 42 acts as a support for a deformable element and/or an intervention element which is directed in the plane of the beam at the suitable angle 48.

In one an embodiment, the distal movable arm 42 can be the intervention element.

The second longitudinal guiding device comprises a rail 140 which is attached to the external surface of the catheter 1. Preferentially, the rail 140 is collinear to the main axis of the window 3. In one mode, their axes are the same as previously seen. In another mode, the rail is included in the catheter 1, that is inside the catheter. The latter is then notched in the intervention area of the angular guiding device in order to enable the intervention element to be used.

FIG. 2E represents a rigid arm 41 translating on a "T" shaped rail 140. The rail 140 is integral with the catheter 1.

A "T" shaped rail enables the second deformable element to be perfectly held in the plane P.

One advantage of this arrangement is that both intervention elements located upstream and downstream of the window 3 are located in the plane of the beam 24 and allow for example joint operations on either side of a valve. Consequently, the operations conducted by the intervention elements 13 are visible in real time on a visualization window which recovers the data from the ultrasonic probe 23.

Thus, an operation can be conducted on a small part of an organ with a great accuracy by means of two deformable elements and two intervention devices.

One advantage consists in having two complementary intervention elements, for example gripping forceps enabling part of the annulus to be caught and a needle enabling the part held by means of the forceps to be pierced. Both interventions can be controlled at any time by the ultrasonic probe 23 which enables a sharp image of the operations to be restored on a screen. Another advantage is to be able, after the puncture, to pick up the suturing wire or the needle that enabled the puncture.

The catheter 1 can comprise different combinations of deformable elements, of their types, of their connections with the catheter 1 and their angular and longitudinal guiding device and the holding devices used for stabilizing the probe or the intervention elements if needs be.

FIGS. 2B to 2D represent in a non-exhaustive way sections of the catheter 1 having different possible combinations of deformable devices and guiding devices.

FIG. 2B represents the case in which a first longitudinal guiding device 74 as a sheath or a port through which the angular guiding device and/or the deformable element and/or the intervention element pass. The longitudinal guiding device 74 includes an axis located in a plane comprising the plane of the beam 24 in a similar way as FIG. 1A. The catheter 1 of FIG. 2B further comprises a rail 140 on which the main arm of a second angular guiding device 40 will be able to pass.

FIG. 2C represents the case in which the main arm, such as the arm 41, of a first angular guiding device and/or the deformable element and/or the intervention element translates on a rail 75 on the part of the catheter 1 diametrically opposite the window 3. When the angular guiding device is used, it is arranged along the rail 75. A second angular guiding device comprises a main arm translating on a rail 140 on the opposite part of the catheter 1, the axis of the rail 140 being the same as the axis of the window 3. The second angular guiding device is then along the rail 140, diametrically opposite the rail 75.

FIG. 2D represents the case in which a first deformable element 10 comprises a distal arm 12 arranged inside the catheter 1 and circulating in a first longitudinal guiding device 74 in the form of a tubular port 74. The axis of the tubular port 74 is located in a plane comprising the plane of the beam 24. In this embodiment, a second deformable element, not represented, for example similar to the first deformable element 10, is arranged inside the catheter 1 and circulates in a second longitudinal guiding device 141 also in the form of a tubular port 141. The axis of the tubular part 141 is also located in a plane comprising the plane of the beam 24.

FIG. 2D represents the case where there is a first tubular port 74 arranged inside the catheter 1 through which a first angular guiding device and/or the deformable element and/or the intervention element pass. In this embodiment, a second angular guiding device and/or the deformable element and/or the associated intervention element are arranged inside the catheter 1 and circulate in a second tubular port 141 coaxial to the ports 74 and 21. These ports each form a longitudinal guiding device.

In this embodiment, the catheter 1 then comprises a first window 4 enabling the first intervention element 13 to be extracted from the catheter 1 and a second window (not represented) upstream of the window 4 enabling a second intervention element, not represented, to be extracted from the catheter 1. Both intervention elements are guided by means of deformable elements and/or angular guiding device(s) and/or longitudinal guiding device(s) similar to those previously described at modifiable intervention angles.

Figure 2F:
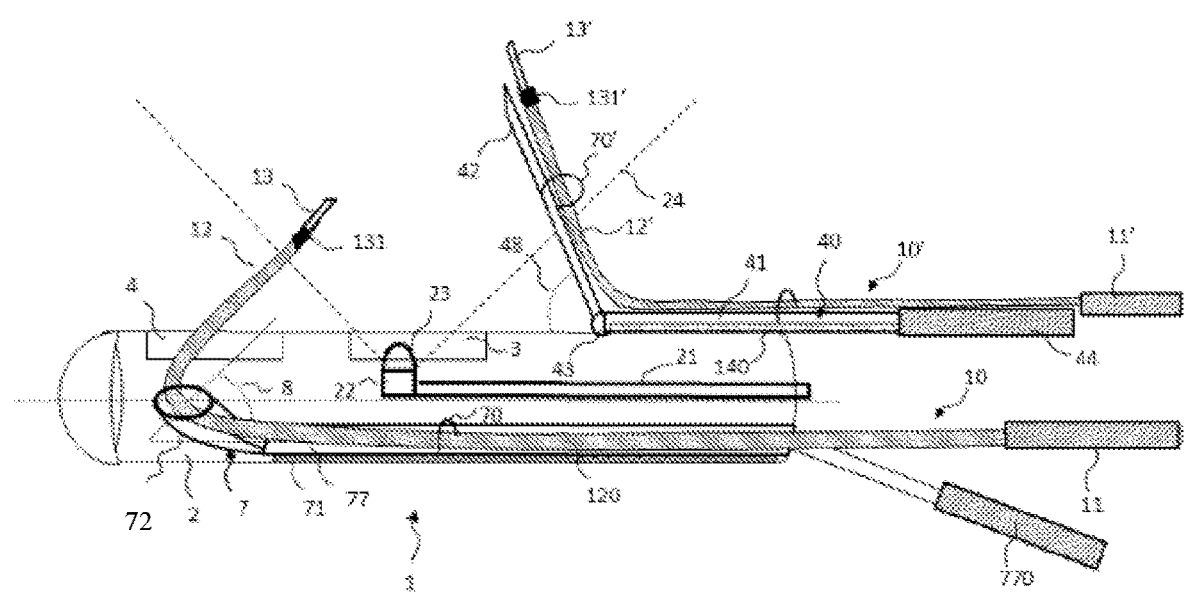

FIG. 2F represents another alternative embodiment in which a rail type longitudinal guiding device 71 is arranged inside a catheter 1. The longitudinal guiding device 71 enables an arm 77 of an angular guiding device 7 to be conveyed into the hollow body 2 of the catheter 1. The main arm 120 of the deformable element 10 the distal arm 12 of which is guided by the distal movable arm 72 of the angular guiding device 7. The arm 77 of the angular guiding device 7 is guided by the longitudinal guiding device 71 and is longitudinally mobilisable such that its distance to the window 4 is controllable by means of a remote driving means 770 such as a handle and a lock screw for example. The arm 10 is longitudinally mobilisable and its distance to the window 4 is controllable by a remote control device 11 such as a handle and lock screw for example.

The probe 23, its head 22 and the arm 21 are represented in FIG. 2E, on the other hand the longitudinal guiding device 20 is not represented as in FIG. 1A.

Figure 2G:
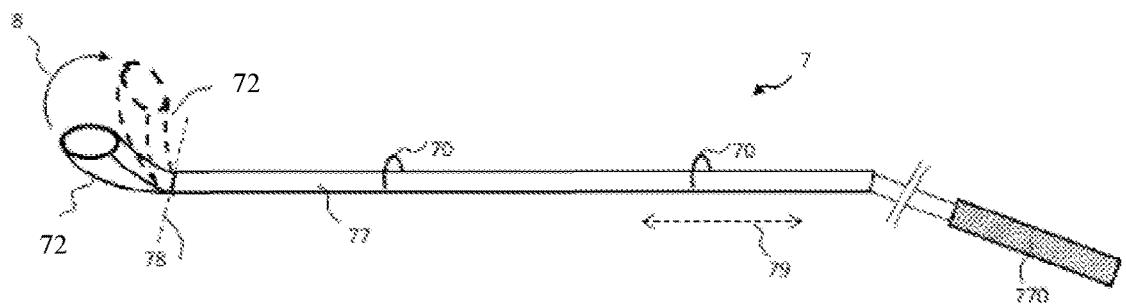
FIG. 2G: an embodiment of a longitudinal guiding device.

FIG. 2G represents two positions of the distal movable arm 72 of the angular guiding device 7 allowing an intervention angle 8 to be controlled. The distal movable arm 72 makes a rotation by an angle 8 about an axis 78. The arm 77 can be a push rod type rail making translational movements 79. The translation of the arm 77 enables the rotation of the distal movable arm 72 to be activated.

The arm 77 has a longitudinal guiding device for the deformable element 10. It can be a rail 71 or a simple guide comprising arches 70 for holding the arm 10.

In the example of FIG. 2G, the angular guiding device 7 comprises a main arm 77, a distal movable arm 72 performing the control of the intervention angle 8 and possibly arches 70 guiding the deformable element 10.

FIG. 2F illustrates a second deformable element 10' having a deformable distal hand 12'. The second deformable element can be for example a sheath inside which a second intervention element 13' is introduced. In another case, the second intervention element 13' is attached to the end of the second deformable element 10' or its distal arm 12'. The second deformable element 10' is longitudinally guided thanks to a longitudinal guiding device 70' which is represented by arches 70' in this exemplary embodiment. The longitudinal guiding device 70' is advantageously integral with the second angular guiding device 40 which enables the rotation of a distal movable arm 42 to be actuated. As previously seen, the second angular guiding device 40 can also include a longitudinal guiding device as a rail 140.

According to one alternative, the distal movable arm 42 can form a deformable element or even an intervention element.

The catheter 1 of the invention provides different combinations of deformable elements on either side of the window 4 depending on the use contemplated.

For example, the second deformable element can be identical to the first deformable element 10 and be held by an angular guiding device 7 analogous to the one represented for the first deformable element 10 of FIG. 1A. In the latter case, two apertures arranged upstream and downstream of the port 3 can be designed so as to allow type 10 deformable elements and/or their type 12' distal arms and/or type 13 intervention elements to be extracted on either side of the beam 23.

Conversely, the first deformable element can be of the same type as the second deformable element 10' of FIG. 2F, that is attached to the external surface of the catheter 1 and be guided by a type 70' longitudinal guiding device or an equivalent and a second angular guiding device 40 such as the angular guiding device longitudinally guided for example thanks to the rail 140. In the latter case, two rails 75 and 140 arranged as represented in FIG. 2C can be used.

When two deformable elements 10, 10' are used in a same catheter 1, they are disposed on either side of the port 3 along the longitudinal axis of said catheter 1. In this case, the evolutions of both intervention elements 13, 13' in the plane of the beam 24 can be recorded and visualized on an imaging generated from the signals collected by the ultrasonic probe 23.

Different embodiments of the deformable elements 10 and 10', whether they are located upstream or downstream of the port 3, can be used in the catheter 1 of the invention.

By way of example, FIGS. 3A, 3B, 3C, 3D represent different embodiments of a second angular guiding device 40 adapted to the catheter 1 of the invention. They can be arranged inside or outside the catheter 1 and comprise a flexible or rigid arm according to the embodiment of the invention.

FIG. 3A represents an exemplary embodiment of the second angular guiding device 40. The end of the second angular guiding device 40 comprises a distal movable arm 42 forming a support for a deformable element 10' or an intervention element 13'. The distal movable arm 42 is illustrated in profile and forms a swinging device. According to the embodiments, the distal movable arm can be considered as being part of the deformable element or also it can define the intervention element according to the contemplated case of use.

A pivot connection 43 allows the end of the second angular guiding device 40 to be rotated about a rotational axis attached to the second angular guiding device 40. The arm 41 can be a push rod which can be actuated by the rotation of a handle 44 and by means of a helical connection 47. The helical connection can be provided by a screw thread system 47. The deformable element 10' is held along the second angular guiding device 40 and in particular up to the end of the distal movable arm 42 by one or more rings 70' as represented in FIG. 2F.

Advantageously, when the distal movable arm is a deformable element, the second angular guiding device 40 and the deformable element include common elements, for example at and beyond the pivot connection 43. This is an advantage from the overall space point of view.

Figure 3B:
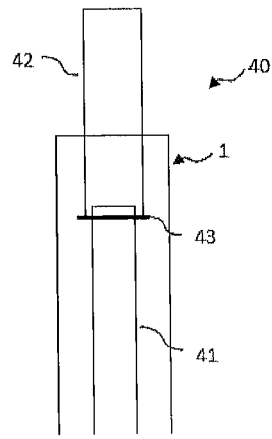

FIG. 3B represents the top view of the second angular guiding device 40 of FIG. 3A when attached to a catheter 1.

Figure 3C:
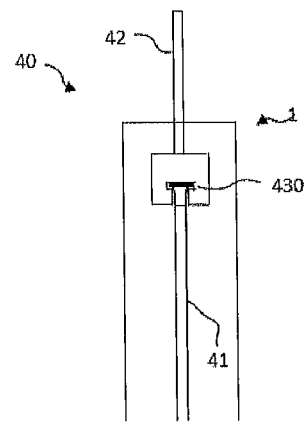

FIG. 3C represents an alternative embodiment of the pivot connection 43 which enables the distal movable arm 42 to be swung in the plane of the beam 24. The pivot connection 430 can go with a slide connection allowed by the translation along the catheter 1 of a movable push rod 41 or only a part of the push rod 41. The translation can be provided by a rod being on a rail attached to the surface of the catheter 1. In this case, the push rod 41 can be hollow and slotted at its distal end to form a connection with the distal movable arm 42.

The rail is then a longitudinal guiding device of an arm of a second angular guiding device 40.

Figure 3D:
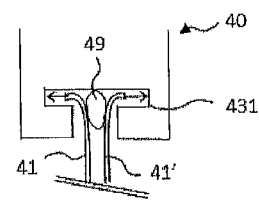

FIG. 3D represents an alternative pivot connection 431 which enables the distal movable arm 42 to be swung. The pivot connection 431 can be provided by means of a side clearance of the rods 41, 41' obtained thanks to an expandable balloon 49. The expandable balloon 49 allows the push rods 41, 41' to be attached and held. The expandable balloon 49 is a holding device for stabilizing a position and orientation. Such a device can also be used for the probe in a removable probe version of the catheter of the invention.

A push rod 41 and a handle 44 can also be combined with a flexible arm 21 for holding the probe 23. This embodiment is not represented in the figures. For example, this system can be used to introduce the probe 23 in the catheter 1 and position it facing the port 3. To prevent a length difference from being generated between the arm 21 and the catheter 1 when the push rod is combined with a flexible arm 21 represented in FIG. 2, it is possible to use a length compensation device.

Indeed, a flexible arm introduced in a catheter 1 can have a curvature different from that of the catheter 1 during these displacements. In this case, a length difference is observed at the distal end or at the port 3.

The length compensation device between a flexible arm and a catheter 1 enables the final position for example of the probe 23 facing a port 3 to be adjusted when such an arm is used with a removable probe. The length compensation device can comprise for example a nut-locknut system.

Such a length compensation device can also be used with a fixed or removable angular guiding device enabling the movements of an intervention element 13 to be controlled.

When the probe 23 is positioned with the proper orientation so as to be facing the port 3 with the proper length, a holding device can be used in the catheter 1 of the invention. For example, a holding device can be a balloon arranged at the distal end of the arm 21 enabling, when inflated, the probe 23 to be blocked in its movements.

FIGS. 4A and 4B represent two positions of another alternative angular guiding device combined with a catheter 1 of the invention. In this mode, the angular guiding device comprises a part 41 inside the hollow body 2 of a catheter 1 which can be for example a wire connecting a remote driving means 44 located on the proximal part of the catheter at the end of the distal movable arm 42 of the angular guiding device located on the distal part. The distal movable arm 42 comprises an end along which a deformable element can be positioned, the latter being able to guide the positioning of an intervention element outside the hollow body of the catheter 1. By way of example, the deformable element 10' and the intervention element 13' of FIG. 2F could be employed together with this embodiment. The deformable element 10' is then held along and/or at the end of the distal movable arm 42 of the angular guiding device by one or more rings as the rings 70' of FIG. 2F.

This embodiment is provided by a remote driving means 44 which can be a control handle 44. A wire 41' is then connected on the one hand to the handle 44 and on the other hand to a distal movable arm 42 that can be for example an intervention element or the end of an angular device acting as a support. A return element 45 for example formed by a spring (as shown in FIG. 4A) is assembled to a pivot connection 43. The return element 45 is integral with the body 2 of the catheter 1. The spring pushes back the distal movable arm 42 of the angular guiding device when it is in a position enabling an operation to be performed, that is in the open position. The handle 44 enables either the wire to be released for the spring to allow the distal movable arm 42 to be deployed, or said distal movable arm 42 to be retained in a closing position thus fighting against the restoring force of the spring. In the open position, a portion of the wire 47 helps the distal movable arm 42 in its rotation. The handle 44 enable the orientation of the distal movable arm 42 and thus of a deformable element and of an intervention element used together with the angular guiding device to be set by setting the portion 47 extending outside a catheter 1.

Advantageously, in this solution, the wire 41' can be connected to the end of the distal movable arm 42 by passing through a window 4'. In this example, the window 4' can be located upstream of the window 3 which lets the beam of the probe 23 through, that is the window 4' is located on the proximal part of the catheter with respect to the window 3. The angular guiding device can comprise a holding element 46 enabling the wire 41' to be acted upon so as to facilitate its translation when extracted from the catheter 1. This mode enables the distal movable arm 42 to be used as a simple axis opened by a spring and held in the closed position thanks to holding a tension on the wire 41'. The handle 44 enables the opening and thus the intervention angle 48 of the distal movable arm 42 and thus of the intervention element to be controlled.

One advantage of the solution of an angular guiding device comprising a wire is that it is less necessary to compensate for the deformations of an arm and its curvatures when introduced in the body of the catheter 1 when the latter is flexible. The wire 41' is already in place when introducing the catheter 1 and is held tensioned by means for example of a handle 44. When the wire is held tensioned, the distal movable arm 42 remains in the closed position and thus the intervention element also remains in the closed position.

A loosening of the wire 41' enables a portion of the wire 47 to be released outside the catheter 1 when the distal movable arm 42 is open. A further clearance of 1 cm or 2 cm of wire enables a sufficient angle aperture 48 to be obtained to deploy the distal movable arm in the plane of the beam 24.

This embodiment can be intended as a so-called "passive" system since the opening of the distal movable arm 42 is carried out by a spring and not by an action of the user.

Conversely, in another alternative embodiment, the spring enables the distal movable arm 42 to be held in the closed position. The opening of the distal movable arm 42 is carried out by an action on a wire 41'. The action can be for example a tension on the wire towards the proximal direction of the catheter 1.

One advantage is that the angular guiding device is already positioned and can be properly oriented by a simple movement of the handle actuating the tension necessary for the wire 41'. This embodiment does not require the setting of its position or its orientation with respect to the window 3.

Another embodiment is the placement of such a second angular guiding device 40 with a control wire 41' at the end of an arm carrying a deformable element 10 or 10' which will use the duct 141 or 74 of the 2D diagram, associated with a longitudinal aperture facing the distal end 42 of the second angular guiding device 40 and upstream of the ultrasound window 3.

One advantage of this solution is to benefit from a smooth surface of the catheter 1, except for the ports for the guiding devices and the deformable elements and the intervention elements. Another advantage is to be able to vary the distance of the pivot connection 43 to modify the position of the deformable element and/or the intervention element in the ultrasonic beam 24.

Alternatively, the same system is positioned at the open end of a hollow tube of the flexible or rigid port 74 or 141 type. Through the port of this tube 74 or 141, a deformable element 10, 10' is positionable up to the end of the second angular guiding device 40 or 7 and beyond. This allows an excellent control of the intervention element 13, 13' which is slid into the deformable element 10 or 10' when this is a sheath. This tube 74 or 141 is included in the catheter 1, and is either fixed, or mobilisable and controllable in its longitudinal movement, for example through a lock screw, in a port or on a rail along the catheter 1 facing the window 4 upstream or downstream of the ultrasonic window 3. In the latter case, the intervention angle is also higher than 90 degrees.

Figure 5A:
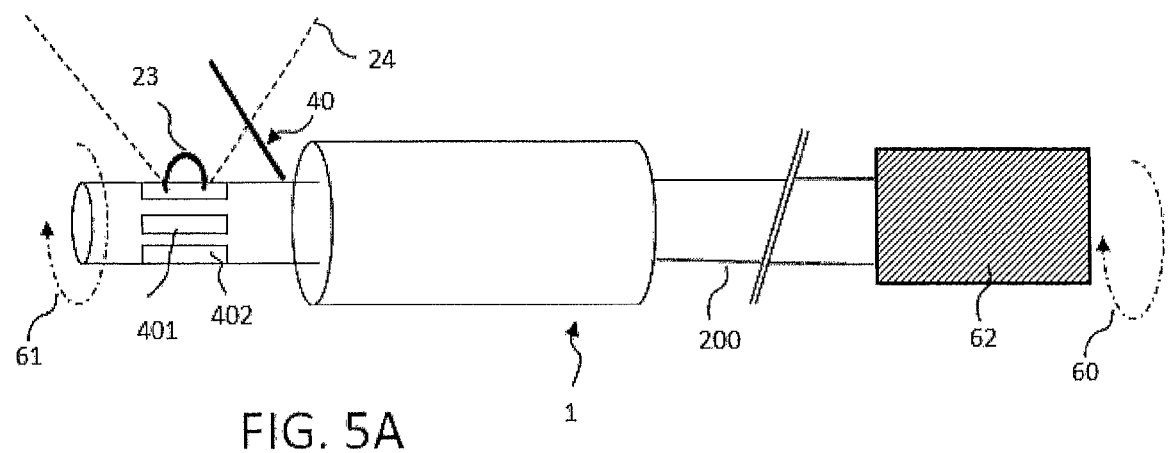
FIGS. 5A, 5B: a catheter of the invention comprising a steerable ultrasonic probe according to one embodiment of the invention.
Figure 5B:
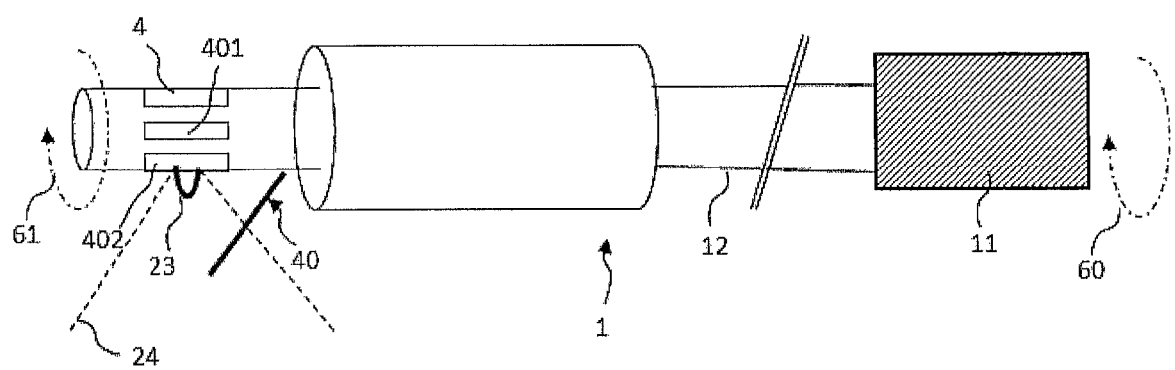

FIGS. 5A, 5B represents an embodiment in which the ultrasonic probe 23 is arranged on a support 200 that can advance in the hollow cavity of the body 2 of the catheter 1. Specifically, according to an alternative embodiment, the support 200 allows a rotational degree of freedom 61 of the probe 23 which can emit a beam in different planes lateral to the catheter 1. The support 200 can be intended as an angular guiding device of the probe 23. A configuration of the arrangement of the probe 23 enables its orientation to be fixed so as to emit in front of a window of the catheter 1. In this embodiment, the catheter 1 comprises a plurality of windows 401, 402 so as to choose the best suitable window for recording actions of the intervention element, not represented, guided by a second angular guiding device 40.

In this embodiment, different deformable elements can be combined with the catheter 1 so as to restrict the overall space of the latter about a single window.

The catheter 1 can comprise in this case a plurality of deformable elements of different natures which are disposed upstream and downstream of different side apertures.

A simple rotation of the catheter 1 in front of the organ to be treated enables different intervention elements to be provided. Once the catheter 1 is suitably oriented, the ultrasonic probe 23 can be configured according to an orientation adapted to record the movements of at least one intervention element.

For convenience of reading, the catheter 1 is not represented in the area of the beam in FIGS. 5A and 5B, the apertures being only represented on the support 200. For further convenience, a single deformable element is represented whereas each aperture can be associated with such a deformable element. According to alternative embodiments, the support can be fully open at the head of the probe 23, the apertures being then present only on the surface of the body 2 of the catheter 1.

When the arm 21 of the ultrasonic probe 23 is flexible, a hinge system can be combined with the arm 21 enabling it to actuate a rotation about its longitudinal axis. The hinge system can comprise for example one or more guide wires connected to the distal end of the arm 21 to drive the rotation of the probe. A roller system can be used to facilitate the rotation of the arm from the wires. There can be two wires so as to initiate a rotation in a first direction and a rotation in a second direction.

The wires can be wound on a notched wheel at the proximal end, that is close to the handle for controlling the arm. The notched wheel or any other equivalent device enables the necessary rotation of the probe to be carried out and a tightening of the wires to be carried out so as to stabilize the position of the probe 23. A notched wheel can be combined with a hook enabling a force to be exerted to retain the wire when the same is wound.

The hinge system can also to be applied to a deformable element for example to drive the orientation of the intervention element when the same has to be extracted from the catheter 1 through a window such as the window 4.

Figure 6A:
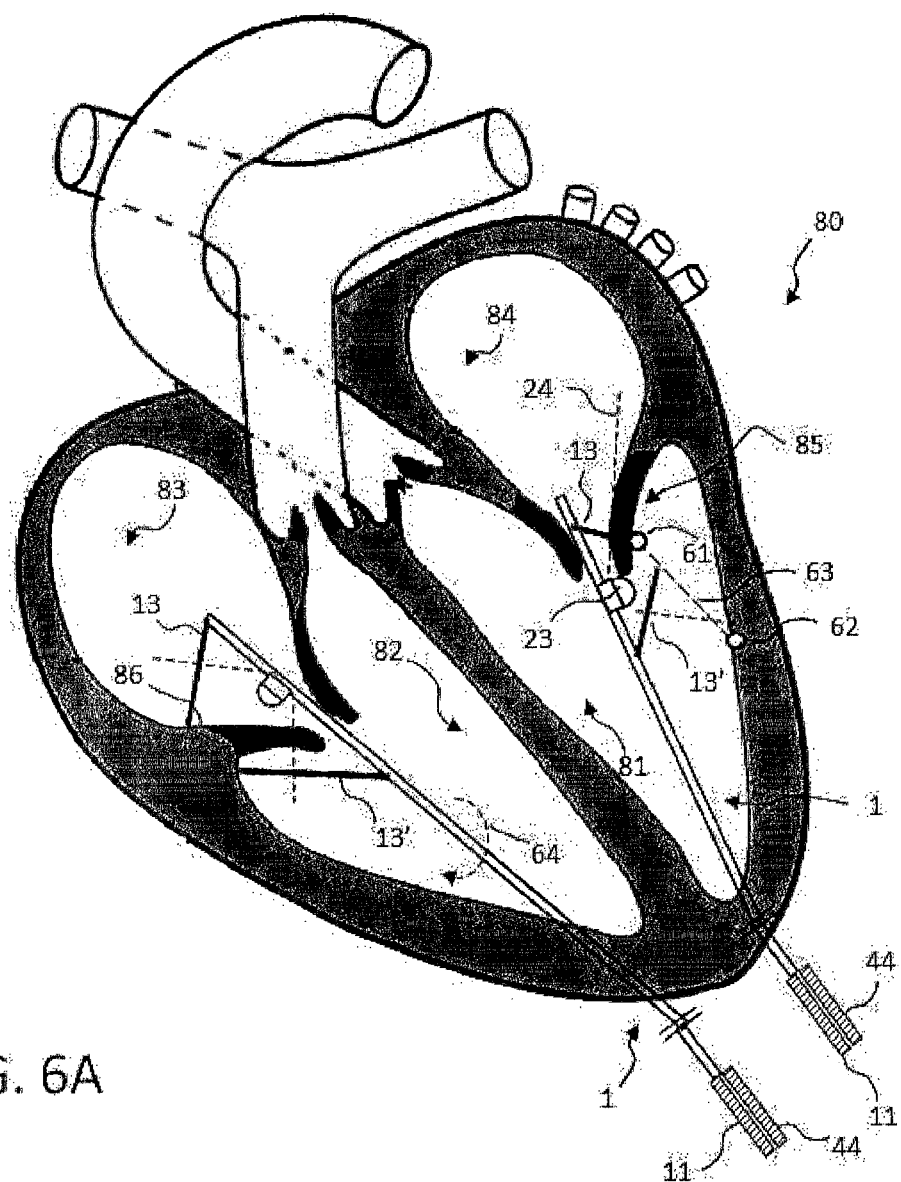
FIG. 6A: two representations of introducing a catheter according to the invention through the left or right atrium for an operation on a mitral or tricuspid valve, respectively of an intervention on the annulus of the right atrioventricular valve and an intervention on the leaflet of the left atrioventricular valve.

FIG. 6A represents a human heart 80 in cross-section comprising a left ventricle 81, a right ventricle 82, a left atrium 84, a right atrium 83. A mitral valve 85 is represented.

FIG. 6A allows a better understanding of two types of interventions which are carried out with a better accuracy and a greater safety for the patient from the catheter 1 of the invention.

A first operation consists in introducing the catheter 1 by perforation of the left ventricle 81 to position the catheter 1 facing the annulus at the base of the mitral valve 85. The introduction of the catheter 1 can be preferentially made in the region of the apex, that is around the tip of the left ventricle.

In this first operation, a catheter 1 of the invention is disposed so as to visualize the mitral valve 85 as well as its annulus and the muscles of the walls. This first operation a field of view to be offered on either side of the valve 85 while allowing the intervention elements 13 and 13' to be handled in the field on either side of the valve 85.

The first operation consists in positioning the window 3 of the catheter 1 so as to visualize the leaflet of the valve 85 in the appropriate area to be treated. A first 13 and a second 13' intervention element are deployed in the plane of the beam. The first intervention element is for example a needle which enables a wire to pass through the valve 85. This wire advantageously carries at its distal end a biocompatible device preventing it from passing through the puncture point on the leaflet. The biocompatible device can be a knot, a clip, a small bulky element such as a rod, a ball, etc. The second intervention element 13' enables the wire 63 to be recovered and attached on a point 62 of the heart muscle wall. Further, the wire 63 can be held at a point 61 of the end of the valve 85 for example by making a knot or adding a system blocking the wire such as a clip, a wire blocking ball, etc. Advantageously, the wire has a needle at each end and is used for making a U point on the leaflet using two punctures.

The valve is thus held at a point 61 of its end by the tensioned wire 63. The wire 63 once it is held on either side thus enables the movement of the leaflet to be controlled and for example avoids a prolapsus thereof.

The first operation thereby required a perforation of the leaflet of the valve 85 to be made and a wire 63 to be passed and attached on a wall of the heart 80.

A second operation can be made by means of the catheter according to the invention. A second operation is represented on the right ventricle 82. It can also be made on the left atrioventricular valve 85 in a similar way.

The catheter 1 is inserted in this example through the apex at the right ventricle so as to be positioned facing the annulus of the atrioventricular valve 86. The distal end of the catheter 1 penetrates the right atrium so as to enable an intervention element 13 to perforate the annulus at a first point of its circumference and introduce a wire therein. The wire is then recovered by the intervention element 13' located on the right ventricle.

Secondly, the catheter 1 performs a rotation along the longitudinal axis of the catheter so as to perforate a second point of the circumference of the base of the annulus to introduce the wire therein. Then, the wire can be tensioned so as to bring the first and second perforation points closer to each other so as to tighten the annulus. The second operation consists in retightening the annular base. Finally, an attachment can be performed for example through making a knot or adding a clip or a system for attaching two wires to each other for example using a rivet.

Figure 6B:
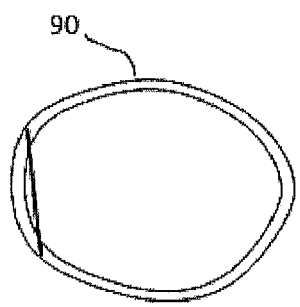
FIGS. 6B and 6C: the result of an intervention on an annulus of a valve after performing a method of the invention.

FIG. 6B represents the base of an annulus 90 perforated at two points connected by a wire.

Figure 6C:
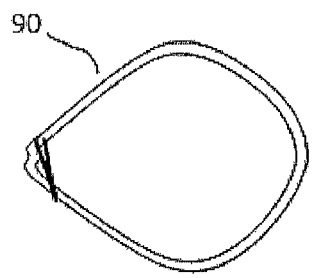

FIG. 6C represents the base of the annulus 90 after the wire has been tightened. It is understood that the apparent surface of the annulus 90 is reduced. This second operation thus enables an annulus to be tightened, this operation can also be intended as an annuloplasty of a heart valve.

According to other possibilities, other perforation points can be made in an annuloplasty operation.

The catheter 1 can be combined with a suction cup for holding the heart. This combination is particularly suitable for operations that involve an introduction of the catheter through the apex of the heart.

The catheter 1 comprises in this embodiment a suction cup, in the centre of the suction cup an aperture enables an operating channel to be introduced, which does not make the suction cup lose its suction feature and for example enables a catheter 1 of the invention to pass therethrough.

The major interest of the suction cup is to stabilize the apex of the heart, to limit the risk of bleeding and of leaving the apex.

The suction cup system can advantageously be associated with a device for controlling the movements of the suction cup by attaching it to a fixed arm (for example attached to the surgical retractor or the operating table). Likewise, in this situation, the catheter 1 is advantageously connected to a device for controlling the longitudinal movements through the suction cup and the angular movements about the puncture point on the apex of the heart. The mobilization of the catheter 1 longitudinally and angularly is made through three guiding devices, the first one controlling the longitudinal movements and the other two controlling the rotation of the proximal part of the catheter 1 along two arcs of circle perpendicular to each other and centred on the puncture point at the apex of the ventricle.

Further, the invention relates to a method for operating on an area of the heart from the catheter 1 of the invention as previously discussed in light of FIGS. 6A, 6B, 6C. This method relates to the use of the invention for making a corrective action on one or more heart atrioventricular valves, also called mitral and tricuspid valves. The invention in particular allows an annuloplasty, corresponding to a plastic surgery of the annulus, and a valvuloplasty, which corresponds to a plastic surgery of the valve itself to be made in combination, that is the leaflets and/or the sub-valvular apparatus. The invention also enables the two later plastic surgeries to be independently made: plastic surgery of the annulus on the one hand and plastic surgery of the leaflets or of the sub-valvular apparatus of the valve on the other hand.

The purpose of the method of the invention is to allow the annuloplasty and the plastic surgery of the leaflet to be easily made without any risk regardless of the mode.

The method of the invention takes advantage of the alignment on the same instrument of the ultrasonic cells creating the ultrasound beam and an intervention element swinging in the plane of the ultrasonic beam. It is then possible to visualize in this beam the displacements of the intervention element. This enables in the same time the valve annulus to be visualized with its connections with the atrial and ventricular cavities, as well as the instrument, such as a needle or forceps for example, desired to be used at the valve annulus.

Methods

The method of the invention is compatible with two different operating modes. Either the catheter of the invention arrives at the valve by the atrial antegrade route, or by the ventricular retrograde route.

Let us consider the first operating mode by introducing the catheter through the atrial antegrade route. This approach can be either direct by puncture of the atrial wall, or by a remote venous percutaneous access and transeptal puncture. In the latter case, the puncture can be made at a peripheral vein such as for example the femoral vein or the jugular vein. This solution favours the use of a catheter of the invention in its flexible version.

In this first mode, the catheter 1 reaches the mitral or tricuspid valve in the physiological direction of the blood stream.

When the catheter reaches the atrium, it is pushed under radioscopy or ultrasonography control into the valve port and stabilized at this level so as to be able to visualize the valve annulus on the ultrasonographic image it produces. At this time, it is possible using at least one intervention element of the catheter of the invention to place the instrument that will reach the valve annulus. The device of the invention also enables in its favoured mode to have two available deformable elements allowing two action types to be simultaneously conducted on the valve annulus. According to one case, an intervention element can be a needle enabling this annulus to be perforated and a transfixing suture to be installed. The second deformable element, such as 12', makes it possible the capture of the needle and/or any element passed through the hole created by the transfixing needle. Other intervention elements such as those previously mentioned can be used.

The intervention element of the catheter 1 of the invention can be located either proximally, or distally with respect to the ultrasonic beam, or together on either side of the ultrasonic beam. Once the first suture is placed, the distal end of the instrument is rotated a few degrees so as to be able to place a second suture. Thereby little by little, it is possible to place successively all along the valve annulus one or more suture(s) which can be used to perform the annuloplasty. The annuloplasty is materialized by an operation of tightening and/or bringing the sutures closer to each other and/or using these sutures to attach a prosthetic annulus.

Let us consider a second operating mode, in which the catheter 1 is introduced by the retrograde route.

This approach is made through the ventricular apex (or a region close to the apex) as represented in FIG. 6 on the side wall of the left ventricle. The principle is the same as the first operating mode given that also in this case the intervention element can be located at the proximal or distal position with respect to the ultrasonic cells.

When the catheter reaches the ventricle, it is pushed under radioscopy or ultrasonography control in the valve port and stabilized at this level so as to be able to visualize the valve annulus on the ultrasonographic image it produces. At this time, it is possible using an intervention element of the catheter of the invention to place the instrument that will reach the valve annulus. As previously, the intervention element can be for example a needle enabling this annulus to be perforated and a transfixing suture to be installed. Likewise, a second deformable element, such as 12', makes it possible the capture of the needle and/or any element passed through the hole created by the transfixing needle.

Other intervention elements such as those previously mentioned can be used. The intervention element can be located either proximally, or distally with respect to the ultrasonic beam generated. Once the first suture is placed, the distal end of the instrument while remaining in the valve port is rotated a few degrees so as to be able to place a second suture. Thereby little by little, it is possible to place successively all along the valve annulus one or more suture(s) which can be used to perform the annuloplasty. As previously set forth, the annuloplasty is materialized by an operation of tightening and/or bringing the sutures closer to each other and/or by using these sutures to attach a prosthetic annulus.

In both approaches, it is possible to use the catheter 1 of the invention to perform a diagnostic or therapeutic action on the leaflets themselves. It is also possible to visualize and reach, using one of the intervention element(s) of the catheter of the invention any point of the valve. The intervention element, depending on its nature, enables the valve to be caught with forceps and/or to attach a suture thereto and/or to perform any therapeutic or diagnostic action therein. The whole is made with a perfect ultrasonographic control of both positioning the leaflet, in particular of the distance between the free edge and the valve annulus, and also the depth of the valve tissue, whether it is transfixing or not.

The placement of one or more sutures on the mitral or tricuspid annulus from the catheter of the invention can also be used to suture or hold in place a valve replacement substitute introduced by the mini-invasive or percutaneous arrival. This solution enables a major problem caused during percutaneous valve replacements to be overcome: obtaining an accurate positioning astride the valve annulus and setting an attachment in place of the percutaneously inserted valve.

Besides, the invention enables the para-prosthetic leaks to be reduced thanks to a proper hold of the valve in place and to the application of the native valve annulus to the prosthetic substitute.

The treatment of the aortic and pulmonary valves can also be contemplated with this invention by allowing points on the aortic or pulmonary annulus, as well as on the aortic or pulmonary wall to be accurately placed.

The treatment of abnormal communications between the heart cavities can also be contemplated with this invention.

According to one embodiment of the invention which can be combined with all the preceding modes, the cells generating the ultrasonographic beam can be replaced with a matrix which will generate a volume 3D image. The imaging principle remains analogous to obtaining an image along a planar beam and the method of the invention comprises the same steps. The advantage is to allow a better definition of the anatomic elements located around and remote from the working plane of the intervention element.

The invention claimed is:

1. A catheter comprising:
   a hollow body extending longitudinally;
   at least three guides aligned in a first plane, which are collinear to an axis of the catheter, a first guide being able to guide longitudinally a removable probe and a second and a third guides being each able to guide at least longitudinally an angular guiding device and/or a deformable element and/or an intervention element, the first guide opening into a first side window of the body of the catheter, the second guide opening into upstream of the first side window and the third guide opening into downstream of the first side window, and
   at least one steerable angular guiding device associated with one of the second and third guides and the rotational movements of which are included in the first plane.

2. The catheter according to claim 1, further comprising at least one side aperture the largest dimension of which is included in a same plane as the largest dimension of the first side window, the second or the third guide opening into the side aperture of the catheter.

3. The catheter according to claim 1, wherein at least one of the second and/or third guide(s) comprises a longitudinal rail integral with the body of the catheter.

4. The catheter according to claim 1, wherein one of the second and/or third guide(s) comprises a tubular port extending longitudinally inside the hollow body of the catheter.

5. The catheter according to claim 1, further comprising an irrigation channel inside the catheter a flow rate of an irrigation fluid of which is controllable by means of a fluid control device.

6. The catheter according to claim 1, wherein the catheter is configured to cooperate with an introducer including a suction cup at its proximal end to adhere by suction to an organ to be perforated, said introducer including an operating channel enabling said catheter to pass inside said organ.

7. The catheter according to claim 1, wherein the suction cup comprises a centre operating channel not communicating with the suction part of the suction cup.

\* \* \* \* \*